United States Patent
Platte et al.

(10) Patent No.: US 10,288,551 B2
(45) Date of Patent: May 14, 2019

(54) FLOW-THROUGH MEASURING CELL

(71) Applicant: OPTEK-DANULAT GMBH, Essen (DE)

(72) Inventors: Daniel Platte, Velbert (DE); Peter Schroeren, Kempen (DE); Jurgen Danulat, Mettmann (DE); Andreas Reese, Essen (DE)

(73) Assignee: OPTEK-DANULAT GMBH, Essen (DE)

( * ) Notice: Subject to any disclaimer, the term of this patent is extended or adjusted under 35 U.S.C. 154(b) by 144 days.

(21) Appl. No.: 14/956,937

(22) Filed: Dec. 2, 2015

(65) Prior Publication Data

US 2016/0091414 A1   Mar. 31, 2016

Related U.S. Application Data

(63) Continuation of application No. 14/002,835, filed as application No. PCT/EP2012/053272 on Feb. 27, 2012, now Pat. No. 9,239,285.

(30) Foreign Application Priority Data

Mar. 4, 2011   (DE) .................. 10 2011 013 002

(51) Int. Cl.
*G01N 21/03*   (2006.01)
*G01N 21/05*   (2006.01)

(52) U.S. Cl.
CPC ......... *G01N 21/0303* (2013.01); *G01N 21/05* (2013.01); *G01N 2021/036* (2013.01); *G01N 2021/0364* (2013.01)

(58) Field of Classification Search
CPC .... G01N 21/01; G01N 21/03; G01N 21/0303; G01N 21/05; G01N 2021/0321; G01N 2021/0364; G01N 2021/052

(Continued)

(56) References Cited

U.S. PATENT DOCUMENTS 3,498,724 A * 3/1970 Harrower ............... G01N 21/03
356/246
3,614,243 A * 10/1971 Harvey ............. G01N 21/0303
250/429

(Continued)

FOREIGN PATENT DOCUMENTS

CN    1989342 A   6/2007   ............... A61F 2/78
DE    2041256      3/1971   ............. G01N 21/03

(Continued)

OTHER PUBLICATIONS

Office Action issued in corresponding Chinese Patent Application No. 201280011655.8, dated Apr. 2, 2015.

(Continued)

*Primary Examiner* — Peter J Macchiarolo
*Assistant Examiner* — Nathaniel J Kolb
(74) *Attorney, Agent, or Firm* — Kusner & Jaffe

(57) ABSTRACT

A flow-through measuring cell having one inlet opening for entry of the fluid, and one outlet opening for exit of the fluid. A single measurement space is located between the inlet opening and outlet opening. A radiation measurement region is provided for measuring the interaction of the fluid in the measuring cell with electromagnetic radiation from outside the measuring cell. The radiation measurement region is bordered by two opposite windows of which one is intended for inlet and the other for exit of the electromagnetic radiation. The measuring cell has a positioning range with several operating positions with a different distance A, A' between the windows into which the measuring cell can be set without rotation.

6 Claims, 5 Drawing Sheets

(58) Field of Classification Search
USPC .......................................................... 356/246
See application file for complete search history.

(56) References Cited

U.S. PATENT DOCUMENTS

| | | | | |
|---|---|---|---|---|
| 3,679,315 A | | 7/1972 | Laucournet et al. ......... | 356/180 |
| 3,810,695 A | * | 5/1974 | Shea ..................... | G01N 21/05 |
| | | | | 356/246 |
| 5,044,747 A | * | 9/1991 | Anthony ................. | G01N 21/03 |
| | | | | 356/246 |
| 5,239,860 A | * | 8/1993 | Harris ................. | G01N 21/3577 |
| | | | | 123/1 A |
| 5,351,686 A | * | 10/1994 | Steuer ................ | A61B 5/14535 |
| | | | | 600/310 |
| 5,371,020 A | * | 12/1994 | Frischauf ........... | G01N 21/0303 |
| | | | | 356/246 |
| 5,510,621 A | * | 4/1996 | Goldman ............... | G01N 21/51 |
| | | | | 250/339.12 |
| 5,905,271 A | | 5/1999 | Wynn ............................ | 250/573 |
| 6,069,694 A | | 5/2000 | VonBargen ................... | 356/246 |
| 6,246,474 B1 | * | 6/2001 | Cerni ..................... | G01N 15/02 |
| | | | | 356/246 |
| 9,239,285 B2 | * | 1/2016 | Platte ................. | G01N 21/0303 |
| 2008/0138261 A1 | * | 6/2008 | Bogner ................. | G01N 21/05 |
| | | | | 422/266 |
| 2008/0252881 A1 | | 10/2008 | Yakimoski et al. .......... | 356/246 |
| 2008/0317627 A1 | * | 12/2008 | Shirai ................... | B01L 3/5025 |
| | | | | 422/52 |
| 2012/0184722 A1 | * | 7/2012 | Samper ................. | G01N 21/05 |
| | | | | 534/10 |
| 2014/0375997 A1 | * | 12/2014 | Gilan ................. | G01N 21/0303 |
| | | | | 356/440 |

FOREIGN PATENT DOCUMENTS

| | | | | |
|---|---|---|---|---|
| DE | 2414162 | | 10/1974 | ............. G01N 21/85 |
| WO | WO 2011/044474 | * | 4/2011 | |

OTHER PUBLICATIONS

Int'l Search Report from corresponding PCT/EP2012/053272 (Form PCT/ISA/210); 2 pages.

* cited by examiner

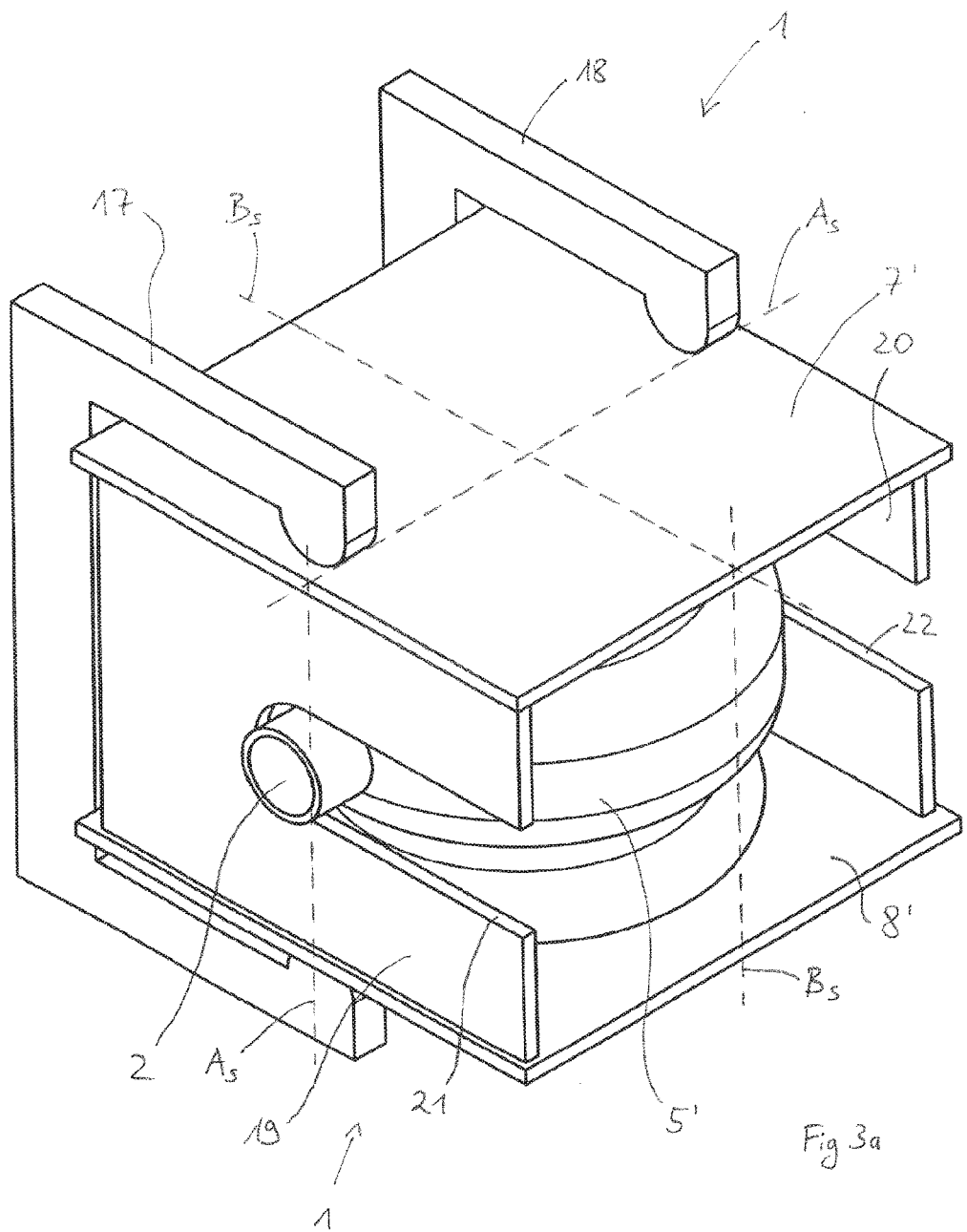

FLOW-THROUGH MEASURING CELL

RELATED APPLICATIONS

The present application is a continuation of U.S. application Ser. No. 14/002,835, filed Sep. 3, 2013, which is a U.S. National Stage Application of International Application No. PCT/EP2012/053272, filed Feb. 27, 2012, which claims priority from German Patent Application No. 102011013002.0, filed Mar. 4, 2011, said patent applications hereby fully incorporated herein by reference.

FIELD OF THE INVENTION

The invention relates to a flow-through measuring cell.

BACKGROUND OF THE INVENTION

To measure the interaction of electromagnetic radiation with fluids in a measuring cell, there must be permeable and transparent windows in the measuring cell for the region of the electromagnetic spectrum which is relevant to the measurement. The windows must seal a measurement space of the measuring cell relative to the environment, even at possibly higher pressures. This applies especially to inline measuring cells.

In particular for absorption measurements it is necessary to know exactly the resulting layer thickness or the optical path length along the beam path of the electromagnetic radiation in order to be able to evaluate the measured values accordingly.

In many measurement applications it is necessary to clean the measuring cell often and/or to make available another layer thickness. In the past, different measuring cells were used for this purpose or various inserts for different layer thicknesses were provided.

U.S. Pat. No. 5,905,271 discloses a measuring cell with a complex mechanical structure in which the adjustment of the optical path length, therefore of the distance between the windows, is enabled in a very small region (by compression of the seal 31 on the stop 22).

SUMMARY OF THE INVENTION

The object of this invention is to devise a measuring cell which can be economically produced and which can be flexibly used.

Advantageous developments of the invention are given in the dependent claims. All combinations of at least two of the features given in the specification, the claims and/or the figures also fall within the scope of the invention. At the given value ranges, values within the indicated limits will also be considered to be disclosed as boundary values and will be claimed in any combination. To avoid repetitions, features disclosed for the system are also to be considered to be disclosed and claimed for the device. Likewise features disclosed for the device are also to be considered to be disclosed and claimed for the system.

The invention is based on the idea of making at least one of the windows located in the beam path settable, or at any time adjustable, without adjustment attachments on the measuring cell or on the measuring cell body along the beam path during installation so that (one-time) setting or adjustment of the distance A, A' between the windows is enabled at least in an adjustment state of the measuring cell, especially for a given temperature range. In other words: The measuring cell has several operating positions to which the measuring cell can be set or adjusted. This measure makes it possible to produce a measuring cell with minimum costs since a wide range of distances A, A' (corresponds especially to the optical path length of the measuring cell) along the adjustment range can be set, especially during installation. During or after installation and setting, the window or windows can be fixed so that adjustment is no longer necessary.

When an adjustment capacity is provided (thus without fixing of the windows) it is no longer necessary to replace the measuring cell to change the layer thickness or at least to replace an insert of the measuring cell. The user can set the distance A, A' within a positioning range at will.

The construction of the measuring cell calls for the setting/adjustment to be able to take place without rotation. A complex mechanism is avoided in this way. Stops for limiting the movement can also be omitted.

It is especially conceivable to provide the windows as claimed in the invention in a basic form which can be produced especially easily. Shaping of the outside contour, especially of stops and the like, can be omitted. In particular the outside contour of the windows is flat or without shoulders or in any cross section rectangular along the beam path. Transversely to the beam path the window can have a circular cross section with an identical diameter over the entire window length (optionally aside from a bevel on the face sides of the window). The window, in one version which can be produced especially easily, has the shape of a round cylinder. Alternatively the simple basic shape can also consist in a plate-shaped configuration with a cross section which is rectangular to the beam path.

In other words, the operating position can be set by application of a compressive force to the windows in the direction of the beam path exclusively from outside of the measuring cell, optionally in combination with a spacer element between the windows to limit the movement. Exclusively from outside means that on the measuring cell itself there are no mechanical means for applying pressure.

In one advantageous embodiment of the invention it is provided that the measuring cell after setting of a first operating position is adjustable within the positioning range, especially without mechanical positioning means attached to the measuring cell (1, 1'), preferably exclusively in the direction of the opposite window.

To the extent the measuring cell is formed from plastic at least on the window receiver, especially the predominant part of the measuring cell, preferably essentially the entire measuring cell, economical production of the measuring cell is possible. Moreover the measuring cell can be made as a disposable measuring cell. Moreover at least one of the windows can be made in a force fit/press fit so that the distance A, A' can be set along the force fit and at least in the direction of the opposite window is easily adjustable by pressure from the outside. This simplifies the installation since with identical measuring cells different optical path lengths can be implemented. In the installation of the measuring cell the set distance A, A' (or the optical path length) can be fixed and identified accordingly, especially by a coding of the measuring cell.

It is also conceivable as claimed in the invention that the operating position can be set or adjusted along one fit of the window or one window receiver which accommodates the window in the measuring cell, preferably by direct fitting of the window relative to the guide channel of the measuring cell or of the measuring cell body, which channel is made especially as shaping of the measuring cell wall. Fitting takes place relative to the inlet or outlet openings and has a tolerance at which the window at least during installation can be moved along the beam path by applying pressure from outside the measuring cell.

At the same time the tolerance of the fit ensures sealing of the measurement space relative to the vicinity of the measuring cell, especially without special sealing means (such as gaskets). The nominal diameter of the fit is the same along the adjustment range.

In this connection one or both windows can be adjustable to one another along their alignment, especially along one window receiving channel which corresponds to the outside contour of the window, preferably by frictional engagement in the channel. To the extent the two windows are adjustable, a larger adjustment range can be implemented. The frictional engagement is caused by the corresponding fit of the window or of the window receiver. The window receiver channel preferably has parallel channel walls in the adjustment range.

According to another advantageous embodiment of the invention it is provided that the positioning range extends from the smallest settable distance A, A' at least by a factor of 1.5, especially at least by a factor of 2, preferably at least by a factor of 3 of the smallest settable distance A, A'. The larger the adjustment range, the more flexibly the measuring cell can be used.

According to one alternative embodiment of the invention it is advantageously provided that at least one wall which borders the measurement space can be flexible deformed along the alignment of the windows and a spacer element for fixing the plane of the window at a distance which is dictated by the choice of the spacer element outside the measurement space can be inserted between the windows. An especially large adjustment range can be implemented by these embodiments.

Here it is especially advantageous if the wall is made as bellows.

An independent invention is a system composed of the above described measuring cell with several spacer elements of different length for setting a distance A' which is defined by the respective spacer element. This makes it possible to offer a set with different stages for defined optical path lengths or distances A'. The user can use the set for correspondingly different application conditions without keeping various measurement cells in reserve.

To the extent the spacer element/elements are made as U-shaped sections, the installation of the measuring cell, especially during adjustment, is facilitated. It is especially advantageous that it is not necessary to intervene in the measurement space or to open the measurement space when the distance A changes.

To the extent at the same time the wall is located, especially fixed on one of the windows, forming a seal, to seal the measurement space, the wall performs a double function, as a result of which additional components such as gaskets, etc. are superfluous.

Other advantages, features and details of the invention will become apparent from the following description of preferred exemplary embodiments and using the drawings.

BRIEF DESCRIPTION OF THE DRAWINGS

FIG. 3a shows a perspective view of a third embodiment of a measuring cell as claimed in the invention, FIG. 3b shows a cross sectional view of the embodiment according to FIG. 3a along one sectional plane $A_S$ and FIG. 3c shows a cross sectional view of the third embodiment along one sectional plane $B_S$ from FIG. 3a.

DETAILED DESCRIPTION OF THE INVENTION

In the figures the same elements and elements with the same functions are identified with the same reference numbers.

Figure 1:
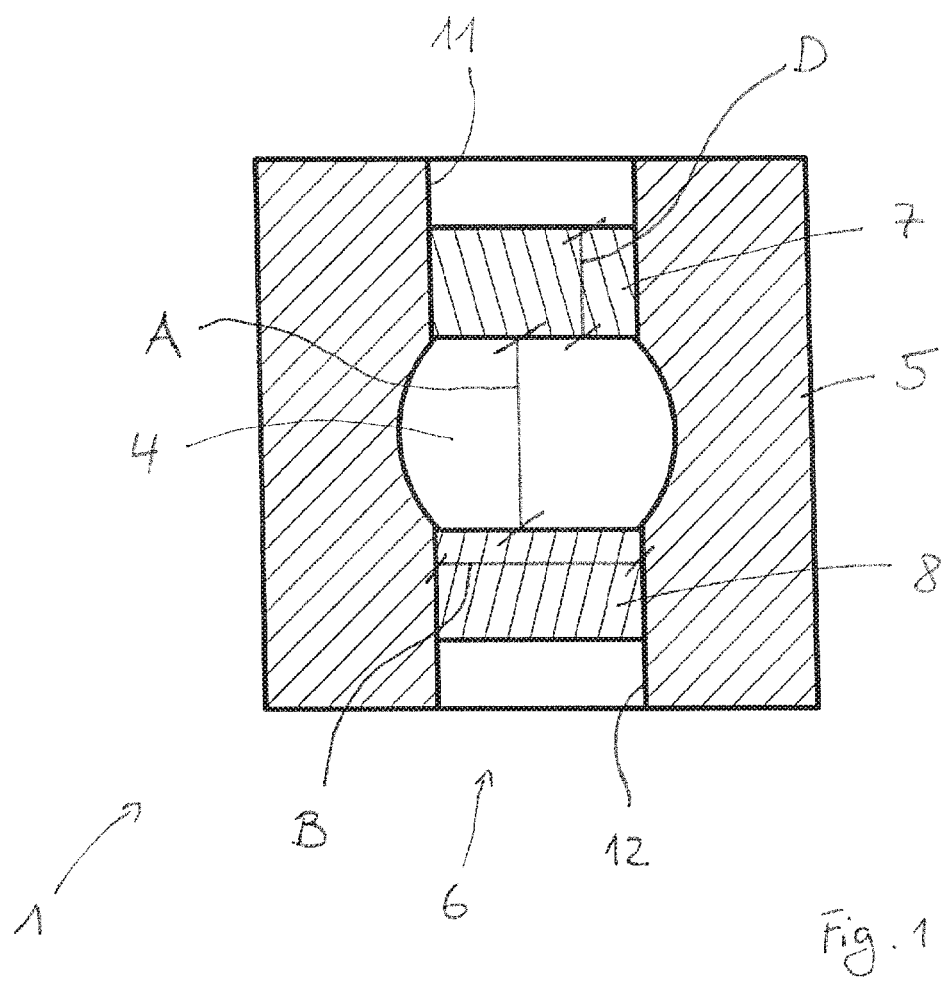
FIG. 1 shows a cross sectional view of a first embodiment of a measuring cell as claimed in the invention.

FIG. 1 shows a measuring cell 1 through which a fluid can flow and which has the measurement space 4 which is bordered by a measuring cell body 5. A fluid flows through the measurement space 4; the interaction of the fluid with electromagnetic radiation, especially light from a light source, is to be measured.

For this purpose there is a radiation measurement region 6 on which electromagnetic radiation is routed through the fluid transversely to the flow direction of the fluid from a radiation source which is not shown, especially a light source. The electromagnetic radiation is measured on the opposite side.

In the beam path (beam direction transversely to the flow direction) there are windows 7, 8 in order to allow the passage of the electromagnetic radiation through the measurement space 4 into the fluid. The windows 7, 8 are each routed in the guide channels 11, 12 whose inside contour corresponds to the outside contour of the windows 7, 8 so that there is a fit between the windows 7, 8 and the respective guide channel 11, 12. This enables an adjustment of the windows 7, 8 along the inside contour of the guide channels 11, 12 so that a distance A between the windows 7, 8 can be set or adjusted. This distance A corresponds especially to the optical path length.

The windows 7, 8 are formed from quartz glass, while the measuring cell body 5 consists of plastic in this exemplary embodiment. The dimensions of the outside contour of the windows 7, 8 and of the inside contours of the guide channels 11, 12 are dimensioned such that the windows 7, 8 at room temperature, therefore at roughly 20° C., can be moved along the guide channels 11, 12 by sliding, even under process conditions, therefore at elevated temperatures, especially greater than 40° C., preferably greater than 60° C., there being frictional engagement between the outside contour of the windows 7, 8 and the respective inside contour of the guide channels 11, 12 so that the windows 7, 8 seal the measurement space 4 relative to the environment even at pressures, especially greater than 3 bar. The tolerance of the fits is made accordingly, the different expansions of the different materials being considered.

To do this it is advantageously provided as claimed in the invention that the windows 7, 8 have a thickness D which is greater than usual at a ratio to a width B of the windows 7, 8. Preferably the ratio D to B is at least 1:10, especially at least 1:5, preferably at least 1:3, even more preferably at least 1:2.

It is also conceivable as claimed in the invention to fix the windows 7, 8 after setting of a distance A in the production/installation of the windows 7, 8 so that adjustment of the windows is precluded. This is especially advantageous when using the measuring cell 1 as a disposable measuring cell.

Figure 2:
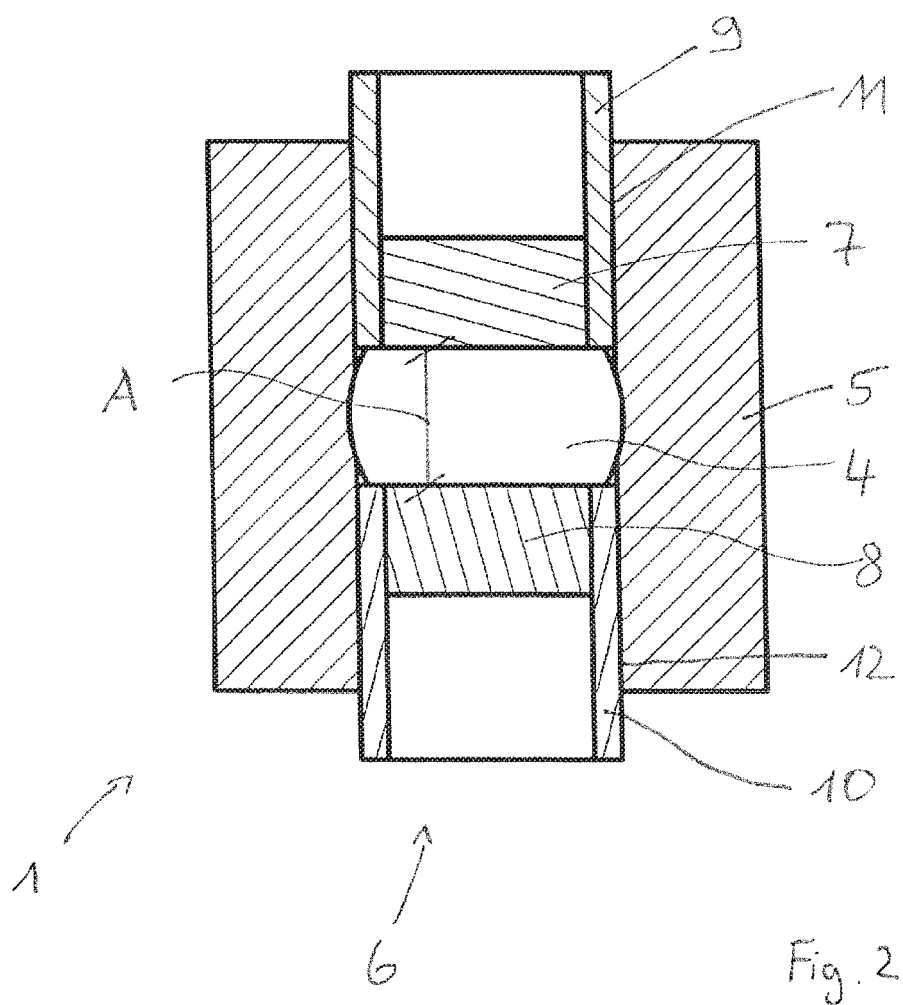
FIG. 2 shows a cross sectional view of a second embodiment of a measuring cell as claimed in the invention.

In the second embodiment which is made very similarly to the first according to FIG. 2, in contrast to the embodiment as shown in FIG. 1, there is one window receiver 9, 10 each for accommodating the windows 7, 8. The window receivers 9, 10 are made tubular with an inside contour which corresponds to the outside contour of the windows 7, 8 so that the windows 7, 8 are fixed in the window receivers 9, 10. The windows 7, 8 are each fixed in the window receivers 9, 10 on the end of the window receiver 9, 10 which points toward the measurement space 4, especially flush with the window receivers 9, 10. The window receivers 9, 10 with their outside contour correspond to the guide channels 11, 12 such that the above described interaction between the windows 7, 8 and the guide channels 11, 12 applies as in the first embodiment according to FIG. 1. Both the guide channels 11, 12 and the window receivers 9, 10 as well as the window receivers 9, 10 and the windows 7, 8 have a fit to one another. The fit can be made such that mutual displacement is possible for only one of the two fits. Advantageously the two fits can be made movable, as a result of which a larger adjustment range can be implemented.

By the window receivers 9, 10 on their ends facing away from the windows 7, 8 projecting over the measuring cell body 5 or over the guide channels 11, 12, the adjustment of the distance A between the windows 7, 8 is simplified, especially when the distance A is increased. This is because the window receivers 9, 10 can be gripped on their ends which project above the measuring cell body 5 or the guide channels 11, 12. Using the dimensions of the window receivers 9, 10 along the beam path, the distance A, therefore the optical path length, can be measured and computed and can accordingly be automatically set. In this case it is advantageous if the fit between the guide channels 11, 12 and the window receivers 9, 10 is made movable.

The statements on the first embodiment also apply analogously to the second embodiment.

Figure 3B:
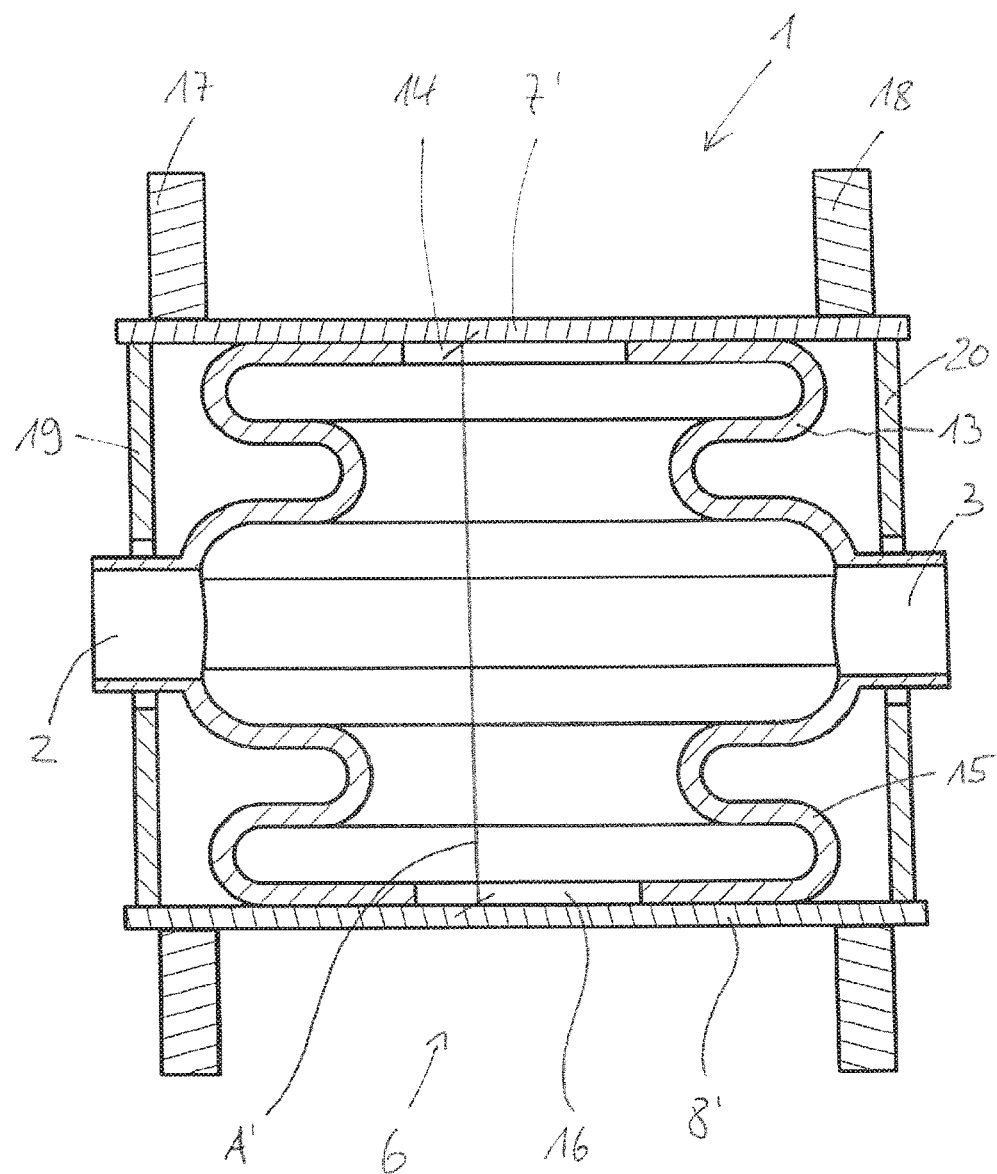
Figure 3C:
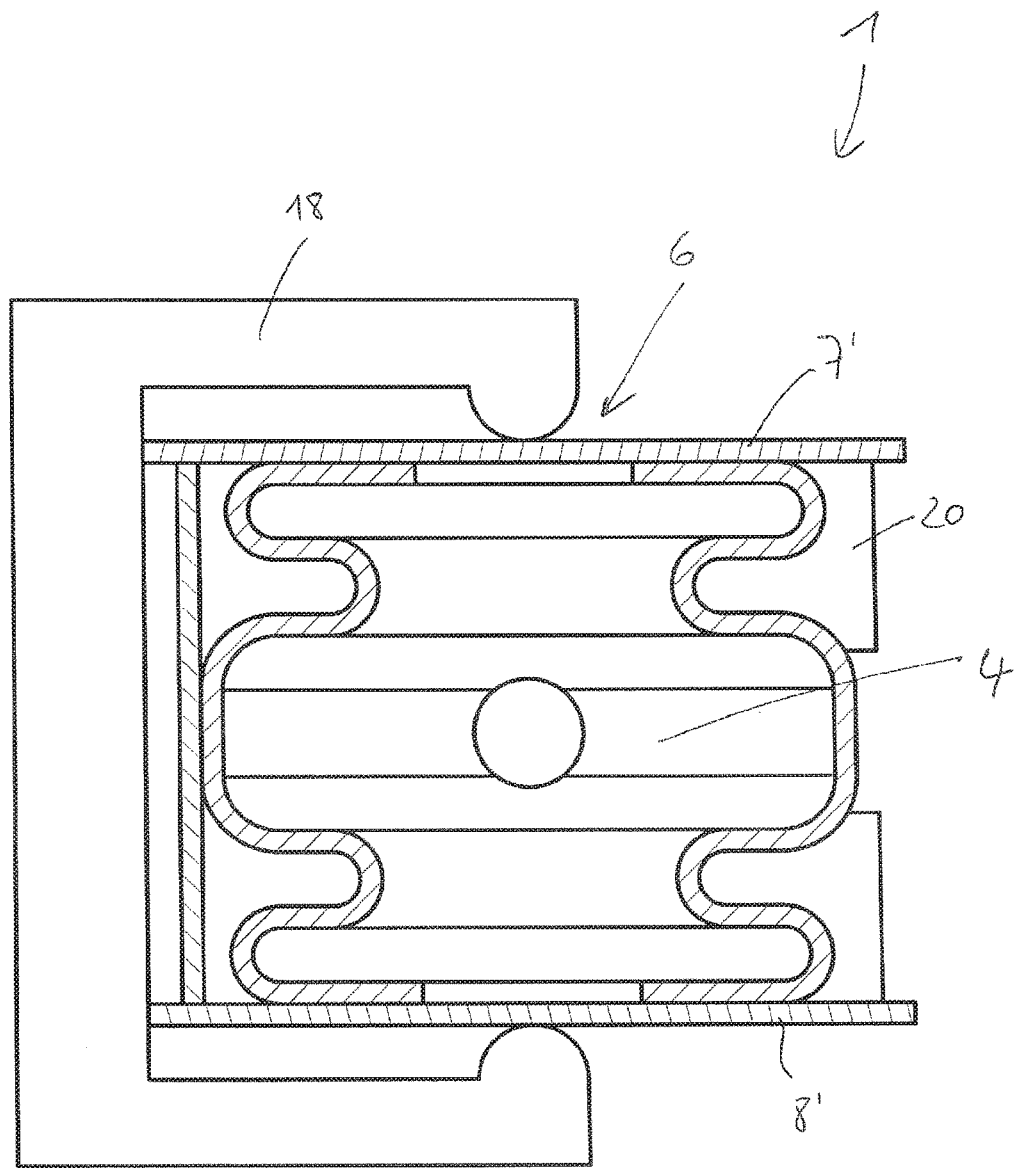

FIG. 3a shows a measuring cell 1' with a measuring cell body 5' which consists predominantly of flexible material, especially rubber. The fluid which is to be measured is routed via an inlet opening 2 into a measurement space 4' and leaves the measurement space 4' via an outlet opening 3 which is shown in FIG. 3b. The inlet opening 2 and the outlet opening 3 have process connections for incorporating the measuring cell 1' into the process line, therefore for inline measurement.

Transversely to the flow direction of the fluid there is a radiation measurement region 6 in which the interaction of the fluid with electromagnetic radiation is measured.

The radiation enters the measurement space 4' through a window 7' and emerges from the measurement space 4' through a window 8' which is located opposite. The electromagnetic radiation is produced by a radiation source which is not shown outside the measuring cell 1' and is routed transversely to the flow direction of the fluid through the measurement space 4' and the windows 7', 8'. On the opposite side, therefore under the window 8' and outside the measuring cell 1', the radiation is detected by a corresponding measuring apparatus, by the interaction with the fluid along the optical path length between the windows 7', 8' the changes which identify the fluid being detectable.

An important aspect of detection is the optical path length which exists by a distance A' between the window 7' and the window 8'.

One wall 13 of the measuring cell body 5' which is made as a peripheral wall is attached to the side of the window 7' which points toward the measurement space 4', especially in the center of the window 7' there being a passage opening 14 so that the electromagnetic radiation can enter the measurement space 4'. A corresponding wall 15 which is made as a peripheral wall and which is located opposite is likewise made flexible. It is accordingly fixed on the window 8' on one side of the window 8' which points toward the measurement space 4' and has a passage opening 16 for exit of the electromagnetic radiation through the window 8'.

The measuring cell body 5' or the measuring cell 1' is fixed by at least one, in this exemplary embodiment two U-shaped spring clips 17, 18 transversely to the flow direction of the fluid. The spring clips 17, 18 extend around the measuring cell body 5' and the windows 7', 8' from the side of the windows 7', 8' facing away from the measurement space 4'.

To fix the distance A' between the windows 7', 8' there is at least one, in this exemplary embodiment two spacer pieces 19, 20 which are clamped outside the measuring cell body 5' as rigid spacers between the windows 7', 8', in particular by the clamping action of the spring clips 17, 18.

Accordingly by replacing the spacer pieces 19, 20 and optionally the spring clips 17, 18 an adjustment range of the distance A' which is limited by the shape of the walls 13, 15 can be implemented so that there is a system consisting of a standard measuring cell 1' and a set of spring clips 17, 18 and corresponding spacer pieces 19, 20.

It is advantageously provided as claimed in the invention that the replacement of the windows 7, 7', 8, 8' is not necessary for adjusting the distances A, A'. The spring clips 17, 18 and spacer pieces 19, 20 which are intended for a defined distance A' can be understood as sets with defined identifications so that replacement can be managed correspondingly easily.

The spacer pieces 19, 20 each have one installation opening 21, 22, especially in which the spacer pieces 19, 20 are made as U-shaped sections so that adjustment of the distance A' is enabled without decoupling of the measuring cell 1 from the process lines.

The function of the spring clips 17, 18 according to one advantageous embodiment which is not shown can be integrated into the spacer pieces by the windows 7', 8' being able to be received into the spacer pieces. The spacer pieces can have corresponding receivers, especially plug grooves, on their tops and bottoms.

| Reference number list | |
|---|---|
| 1, 1' | measuring cell |
| 2 | inlet opening |
| 3 | outlet opening |
| 4, 4' | measurement space |
| 5, 5' | measuring cell body |
| 6 | radiation measurement region |
| 7, 7' | window |
| 8, 8' | window |
| 9 | window receiver |
| 10 | window receiver |
| 11 | guide channel |
| 12 | guide channel |
| 13 | wall |
| 14 | passage opening |
| 15 | wall |
| 16 | passage opening |
| 17 | spring clip |
| 18 | spring clip |
| 19 | spacer piece |
| 20 | spacer piece |
| 21 | installation opening |
| 22 | installation opening |

Having described the invention, the following is claimed:
1. A flow-through measuring cell comprising:
   a measuring cell body defining first and second guide channels;

an inlet opening for entry of a fluid into the measuring cell;

an outlet opening for exit of the fluid from the measuring cell;

a measurement space located between the inlet opening and the outlet opening within a radiation measurement region, the radiation measurement region providing a region for measuring the interaction of electromagnetic radiation, produced by a radiation source outside the measuring cell, with the fluid flowing through the measurement space between the inlet opening and the outlet opening;

a first window that serves as an inlet for the electromagnetic radiation;

a second window, located opposite the first window, that serves as an exit for the electromagnetic radiation;

first and second window receivers that are dimensioned to be respectively received within the first and second guide channels defined by the measuring cell body, the first window receiver dimensioned to receive the first window and the second window receiver dimensioned to receive the second window, wherein an outer surface of the first and second windows respectively engages with an inner surface of the first and second window receivers;

wherein the measurement space is bordered by the measuring cell body and the first and second windows, the first and second windows are respectively received within the first and second guide channels defined by the measuring cell body, at least one of the first and second windows is movable within the respective first and second guide channels to adjust a distance (A) between the first and second windows, thereby providing the measuring cell with a plurality of operating positions within a positioning range, said distance (A) corresponding to an optical path length, there is a frictional fit between an outer surface of the first and second window receivers and an inner surface of the measuring cell body defining the respective first and second guide channels such that a pressure seal is created therebetween, wherein the first and second window receivers each have one end that respectively extends outside of the first and second guide channels, and each of the plurality of operating positions defines a different distance (A) between the first and second windows, the measuring cell adjustable to each of the plurality of operating positions.

2. The measuring cell as claimed in claim 1, wherein at least one of the first and second window receivers is moveable within the respective first and second guide channels of the measuring cell body to move the first and second windows within the respective first and second guide channels, and thereby adjust the distance (A) between the first and second windows.

3. The measuring cell as claimed in claim 1, wherein at least one of the first and second windows is moveable within the respective first and second window receivers.

4. The measuring cell as claimed in claim 1, wherein at least one of the first and second windows is moveable within the respective first and second guide channels by application of a force outside the measuring cell to the first and/or second window receivers.

5. The measuring cell as claimed in claim 1, wherein there is a frictional fit between an outer surface of the first and second windows and an inner surface of the respective first and second window receivers such that a pressure seal is created therebetween.

6. The measuring cell as claimed in claim 1, wherein the measuring cell is adjustable to each of the plurality of operating positions without rotation of the measuring cell.

* * * * *